(12) United States Patent
Haley et al.

(10) Patent No.: US 12,085,552 B2
(45) Date of Patent: Sep. 10, 2024

(54) DEVICE FOR DETECTING HYDROSULFIDE

(71) Applicant: University of Oregon, Eugene, OR (US)

(72) Inventors: Michael M. Haley, Eugene, OR (US); Michael Pluth, Eugene, OR (US); Darren W. Johnson, Eugene, OR (US); Sean Fontenot, Eugene, OR (US)

(73) Assignee: University of Oregon, Eugene, OR (US)

(*) Notice: Subject to any disclaimer, the term of this patent is extended or adjusted under 35 U.S.C. 154(b) by 120 days.

(21) Appl. No.: 17/536,994

(22) Filed: Nov. 29, 2021

(65) Prior Publication Data

US 2022/0082544 A1 Mar. 17, 2022

Related U.S. Application Data

(62) Division of application No. 15/612,848, filed on Jun. 2, 2017, now Pat. No. 11,187,690.

(60) Provisional application No. 62/345,619, filed on Jun. 3, 2016.

(51) Int. Cl.
*G01N 27/414* (2006.01)
*C07C 275/34* (2006.01)
*C07D 213/40* (2006.01)
*G01N 33/18* (2006.01)
*C07C 275/28* (2006.01)

(52) U.S. Cl.
CPC ......... *G01N 33/182* (2013.01); *C07C 275/34* (2013.01); *C07D 213/40* (2013.01); *G01N 27/414* (2013.01); *C07C 275/28* (2013.01); *Y10T 436/156666* (2015.01); *Y10T 436/184* (2015.01)

(58) Field of Classification Search
CPC ........ G01N 27/414; Y10T 436/156666; Y10T 436/184
See application file for complete search history.

(56) References Cited

U.S. PATENT DOCUMENTS

| | | | |
|---|---|---|---|
| 7,803,946 B2 | 9/2010 | Haley et al. | |
| 8,841,460 B2 | 9/2014 | Johnson et al. | |
| 9,664,696 B1 | 5/2017 | Pluth et al. | |
| 2007/0202198 A1 | 8/2007 | Purcell | |
| 2008/0167472 A1 | 7/2008 | Haley et al. | |
| 2009/0184005 A1 | 7/2009 | Zhang et al. | |
| 2009/0280031 A1 | 11/2009 | Serban | |
| 2010/0099683 A1 | 4/2010 | Tomkinson et al. | |

(Continued)

OTHER PUBLICATIONS

"Ionophore," IUPAC. Compendium of Chemical Terminology, 2nd ed. (the "Gold Book"). Compiled by A. D. McNaught and A. Wilkinson. Blackwell Scientific Publications, Oxford (1997). http://dx.doi.org/10.1351/goldbook.IT06772 (Year: 1997).*

(Continued)

*Primary Examiner* — Jennifer Wecker
*Assistant Examiner* — Michelle Adams
(74) *Attorney, Agent, or Firm* — Klarquist Sparkman, LLP

(57) ABSTRACT

A device that includes a polymeric layer, wherein the polymeric layer comprises (A) a polymer and, incorporated within the polymeric layer, (B) a compound, or a protonate or salt thereof, wherein the compound, or a protonate or salt thereof, has a structure that includes at least one moiety configured for reversible, non-covalent binding of the anionic sulfide species.

15 Claims, 6 Drawing Sheets

(56) References Cited

U.S. PATENT DOCUMENTS

2013/0040397 A1* 2/2013 Star .................... G01N 33/0044
977/788
2015/0355153 A1 12/2015 Haley et al.

OTHER PUBLICATIONS

Antonisse, M.M.G. et al. (1998). "Chemically Modified Field-Effect Transistors for Measurement of Ion Activities in Aqueous Solution," In: van den Berg, A., Bergveld, P. (eds) Sensor Technology in the Netherlands: State of the Art. Springer, Dordrecht. pp. 97-105 (Year: 1998).*
Diring,S. et al. "Luminescent Ethynyl-Pyrene Liquid Crystals and Gels for Optoelectronic Devices," J. Am. Chem. Soc. 2009, 131, 18177-18185 (Year: 2009).*
Bailey et al., "Chemiluminescent Detection of Enzymatically Produced Hydrogen Sulfide: Substrate Hydrogen Bonding Influences Selectivity for $H_2S$ over Biological Thiols," *J. Am. Chem. Soc.*, vol. 135, pp. 16697-16704, 2013.
Berryman et al., "Water and hydrogen halides serve the same structural role in a series of 2+2 hydrogen-bonded dimers based on 2,6-bis(2-anilinoethynyl)pyridine sulfonamide receptors," *Angewandte Chemie* 47(1):117-120, 2008.
Butler et al., "Bipyridylacetylenes 1: the synthesis of some bipyridylacetylenes via the palladium-catalyzed coupling of acetylenes with 2,2'-dibromobipyridyl, and the single crystal X-ray structure of 6,6'-bisphenylethynyl-2,2'-bipyridine," *Can. J. Chem.* 69:1117-1123, 1991.
Carroll et al., "Anion-dependent fluorescence in bis(anilinoethynyl)pyridine derivatives: switchable On-Off and Off-On responses," Chemical Communications 47:5539-5541, 2011.
Carroll et al., "Protonation activates anion binding and alters binding selectivity in new inherently fluorescent 2,6-bis(2-anilinoethynyl)pyridine bisureas," *Chemical Communications* 2520-2522, 2009 (Available online Mar. 27, 2009).
Dash et al., "Diarylethynyl amides that recognize the parallel conformation of genomic promoter DNA G-quadruplexes," *Journal of the American Chemical Society* 130(47):15950-15956, 2008 (published online Nov. 4, 2008).
Dash et al., "G-quadruplex recognition by bis-indole carboxamides," *Chemical Communications* 26:3055-3057, 2008.
Droz et al., "Synthesis of highly-functionalized, optically active disaccharide receptors by sequential aryl-alkyne cross-and oxidative acetylenic homo-coupling," *J. Chem. Soc.* 4224-4226, 2000.
Engle et al., "Synthesis and Optoelectronic Properties of 2,6-Bis(2-anilino-ethynyl)pyridine Scaffolds," Chem. Sci. 3:1105-1110, 2012.
Ferrara et al., "Synthesis and Characterization of a Copper(1) Triflate Complex of 1,2:5,6:9,10-Tribenzocyclododeca-1,5,9-triene-3,7,11-triyne," *Organometallics* 6:676-678, 1987.
Ferrara et al., "Synthesis and Characterization of the First Transition-Metal Complex of 1,2:5,6:9,10-Tribenzocyclododeca-1,5,9-triene-3,7,11-triyne," *J. Am. Chem. Soc.* 107:6719-6721, 1985.
Gerhardt et al., "Controlling polymer properties through dynamic metal-ligand interactions: supramolecular cruciform made easy," *Chem. Eur. J.* 13(16):4467-4474, 2007.
Gerhardt et al., "Supramolecular cruciforms," *Chemical Communications* 20:2141-2143, 2006.
Gu et al., "Development of a boron-dipyrromethene-$Cu^{2+}$ensemble based colorimetric probe toward hydrogen sulfide in aqueous media," *Tetrahedron Letters* 52:5000-5003, 2011.
Hancock et al., "Rotaxanes capable of recognizing chloride in aqueous media," *Chem. Eur. J.*, vol. 16, pp. 13082-13094, Oct. 28, 2010.
Hartle et al., "A Synthetic Supramolecular Receptor for the Hydrosulfide Anion," *Angewandte Chemie International Edition*, 55(38): 11480-11484, Aug. 11, 2016. (Abstract only).
Hauck et al., "Phenothiazine Cruciforms: Synthesis and Metallochromic Properties," *Journal of Organic Chemistry* 72(18):6714-6725, 2007.

Jarosz et al., "Microplate-Based Colorimetric Detection of Free Hydrogen Sulfide," *Analytical Chemistry* 85:3638-3643, 2013.
Jia et al., "Novel Phosphorescent Cyclometalated Organotin(IV) and Organolead(IV) Complexes of 2,6-Bis(2'-indolyl)pyridine and 2,6-Bix[2'-(7-azaindolyl)]pyridine," *Organometallics* 22:4070-4078, 2003.
Johnson et al., "Aryl-Acetylene Scaffolding as Receptors in Supramolecular Chemistry," presentation through Department of Chemistry & Materials Science Institute of the University of Oregon, 26 pages, 2007.
Johnson et al., "Synthesis and characterization of pyridine- and thiophene-based platinacyclynes," *Journal of Organometallic Chemistry* 691:413-421, 2006 (available online Oct. 25, 2005).
Lee et al., "Detection of hydrogen peroxide with chemiluminescent micelles," *International Journal of Nanomedicine* 3(4):471-476, 2008.
Leininger et al., "Self-Assembly of Discrete Cyclic Nanostructures Mediated by Transition Metals," *Chem. Rev.* 100:853-908, 2000.
Lippert et al., "Reaction-Based Fluorescent Probes for Selective Imaging of Hydrogen Sulfide in Living Cells," *Journal of the American Chemical Society* 133:10078-10080, 2011.
Liu et al., "A visible light excitable colorimetric and fluorescent ESIPT probe for rapid and selective detection of hydrogen sulfide," *Organic & Biomolecular Chemistry* 12:438-445, 2013.
Liu et al., "Capture and Visualization of Hydrogen Sulfide by a Fluorescent Probe," *Angew. Chem. Int. Ed.* 50:10327-10329, 2011.
Maity et al., "A probe for ratiometric near-infrared fluorescence and colorimetric hydrogen sulfide detection and imaging in living cells," *RSC Advances* 4:11147-11151, 2014.
McGrier et al., "Hydroxy-cruciforms," *Chemical Communications* 21:2127-2129, 2007.
Montoya et al., "Selective turn-on fluorescent probes for imaging hydrogen sulfide in living cells," *Chemical Communications* 48:4767-4769, 2012.
Montoya et al., "Development of Selective Colorimetric Probes for Hydrogen Sulfide Based on Nucleophilic Aromatic Substitution," *J. Org. Chem.*, vol. 78, pp. 6550-6557, 2013.
Nishiyabu, R. et al. "Synthesis, Structure, Anion Binding, and Sensing by Calix[4]pyrrole Isomers," *J. Am. Chem. Soc.*, 128(35): 11496-11504, Aug. 16, 2006.
Palacios, M.A. et al. "A new generation of optical sensor materials," *The Spectrum*, vol. 18 Issue 3, Fall/Winter 2005, pp. 18-20.
Palacios, M.A. et al. "Supramolecular Chemistry Approach to the Design of a High-Resolution Sensor Array for Multianion Detection in Water," *J. Am. Chem. Soc.*, 129(24): 7538-7544, including Supporting Information, May 27, 2007.
Peng et al., "A Fluorescent Probe for Fast and Quantitative Detection of Hydrogen Sulfide in Blood," *Angew. Chem. Int. Ed.* 50:9672-9675, 2011.
Pucher et al., "Structure-Activity Relationship in D-π-A-π-D-Based Photoinitiators for the Two-Photon-Induced Photopolymerization Process," *Macromolecules* 10 pages, 2009.
Qian et al., "Selective fluorescent probes for live-cell monitoring of sulphide," *Nature Communications* 2(495)1-7, 2011.
Roda et al., "Analytical chemiluminescence and bioluminescence: latest achievements and new horizons," *Anal Bioanal Chem* 402:69-76, 2011.
Saha et al., "A colorimetric and fluorometric Bodipy probe for rapid, selective selection of $H_2S$ and its application in live cell imaging," *Organic & Biomolecular Chemistry* 11:8166-8170, 2013.
Sasakura et al., "Development of a Highly Selective Fluorescence Probe for Hydrogen Sulfide," *Journal of the American Chemical Society* 133:18003-18005, 2011.
Shen et al., "Measurement of plasma hydrogen sulfide in vivo and in vitro," *Free Radical Biology & Medicine* 50:1021-1031, 2011.
Tresca, B.W. et al. "Aryl C-H ••• Cl-hydrogen bonding in a fluorescent anion sensor," Chem. Commun., 49(65):7240-7242, Jul. 4, 2013.
Tresca, B.W. et al. "Substituent Effects in CH Hydrogen Bond Interactions: Linear Free Energy Relationships and Influence of Anions," *J. Am. Chem. Soc.*, 137(47):14959-14967, Nov. 5, 2015.

(56) References Cited

OTHER PUBLICATIONS

Van de Bittner et al., "In vivo imaging of hydrogen peroxide production in a murine tumor model with a chemoselective bioluminescent reporter," *PNAS* 107(50):21316-21321, 2010.

Walters et al., "Experimental Studies of Light-Induced Charge Transfer and Charge Redistribution in (X2-Bipyridine)Re(CO)3C1 Complexes," *Inorganic Chemistry* 41:2909-2919, 2002.

Wei et al., "NBD-based colorimetric and fluorescent turn-on probes for hydrogen sulfide," *Organic & Biomolecular Chemistry* 12:479-485, 2013.

Wilson et al., "Switching of Intermolecular Charge Transfer in Cruciforms: Metal Ion Sensing," *Journal of the American Chemical Society* 172(12):4124-4125, 2005.

Wu et al., "A selective colorimetric and ratiometric fluorescent probe for hydrogen sulfide," *Organic & Biomolecular Chemistry* 10:8342-8347, 2012.

Yamaguchi et al., "Evaluation of chemiluminescence reagents for selective detection of reactive oxygen species," *Analytica Chimica Acta* 665:74-78, 2010.

Zhang et al., "A dicopper complex chemiluminescence probe for the determination of thiols in the extracts of murine P388 lymphocytic leukemia cell," *Chem. Commun.* pp. 5624-5626, 2009.

Zhang et al., "Highly selective and sensitive colorimetric probe for hydrogen sulfide by a copper (II) complex of azo-dye based on chemosensing ensemble approach," *Spectrochimica Acta Part A: Molecular and Biomolecular Spectroscopy* 90:35-39, 2012.

Zhang et al., "On-Site Visual Detection of Hydrogen Sulfide in Air Based on Enhancing the Stability of Gold Nanoparticles," *ACS Applied Materials & Interfaces* 6:6300-6307, 2014.

Zhao et al., "A highly selective colorimetric chemodosimeter for fast and quantitative detection of hydrogen sulfide," *Analyst* 137:5576-5580, 2012.

Zucchero et al., "Cruciforms as Functional Fluorophores: Response to Protons and Selected Metal Ions," *J. Am. Chem. Soc.*, vol. 128, pp. 11872-11881, 2006.

Hartle et al., "A Synthetic Supramolecular Receptor for Hydrosulfide Anion," *Agnew Chem Int. Ed. Engl.*, vol. 55(38), Sep. 12, 2016 (12 pages).

* cited by examiner

DEVICE FOR DETECTING HYDROSULFIDE

CROSS REFERENCE TO RELATED APPLICATION

This application is a divisional of U.S. application Ser. No. 15/612,848, filed on Jun. 2, 2017, which claims the benefit of U.S. Provisional Appl. No. 62/345,619, filed on Jun. 3, 2016, which is incorporated herein by reference.

ACKNOWLEDGMENT OF GOVERNMENT SUPPORT

This invention was made with government support under grant CHE-1454747 awarded by the National Science Foundation and grant R01-GM087398 awarded by the National Institutes of Health. The government has certain rights in the invention.

BACKGROUND

Hydrogen sulfide ($H_2S$), although generally known for its toxicity and characteristic odor, is now recognized as an important signaling molecule with diverse biological roles. The biological roles of $H_2S$ range from roles in angiogenesis to wound healing. In mammals, $H_2S$ production is derived primarily from three enzymes: cystathionine-γ-lyase (CSE), cystathionine-β-synthase (CBS), and 3-mercaptopyruvate sulfotransferase (3-MST). The expression of these enzymes in different tissues suggests a broad importance and significance of $H_2S$ in the cardiovascular, circulatory, respiratory, urinary, and nervous systems. Abnormal $H_2S$ regulation, however, has been associated with hypertension, diabetes, as well as various diseases of mental deficiency including Down's syndrome and Alzheimer's disease. In addition to the pathophysiological conditions associated with $H_2S$ misregulation, $H_2S$ can also act on specific cellular targets, including heme proteins, cysteine residues on KATP channels, nitric oxide, and other emerging targets.

Complicating investigations into biological $H_2S$, the $pK_a$ of $H_2S$ (7.0) ensures that both the neutral ($H_2S$) and mono-anionic ($HS^-$) forms are present under physiological conditions, leading to significant and unresolved questions on the specific chemistry and recognition events associated with the individual protonation states. Importantly, these recognition events in sulfide transport rely on non-covalent, reversible interactions with $HS^-$ rather than metal coordination or interaction with the sulfane-sulfur pool.

Despite the importance of $H_2S$, current methods of detection are plagued by irreversibility, which presents a significant problem in developing chemical tools that provide real-time information on biological processes, suggesting a supramolecular (i.e., reversible) approach to hydrosulfide binding would represent an important contribution.

SUMMARY

Disclosed herein is a method for detecting for the presence of $H_2S$ or $HS^-$ anion in a system, comprising contacting a sample from the system with a compound, or a protonate or salt thereof, having a structure represented by:

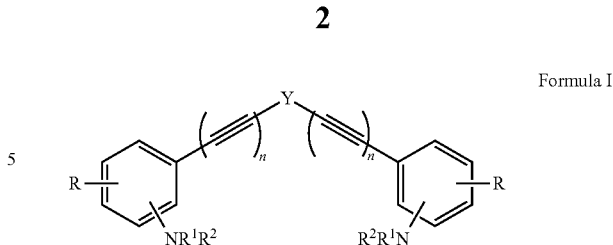

Formula I wherein Y represents an aromatic group or a substituted aromatic group;
n is 1 or 2;
R is independently H, alkyl, substituted alkyl, a polyether moiety, carboxyl, substituted carboxyl, carbamate, substituted carbonate, carbonyloxy, alkoxy, substituted alkoxy, haloalkyl, halogen, nitro, amino, amido, aryloxy, cyano, hydroxyl, or sulfonyl;
$R^1$ is H, substituted lower alkyl, lower alkyl, substituted aralkyl or aralkyl;
$R^2$ is selected from H, acyl, substituted aralkyl, aralkyl, phosphonyl, $—SO_2R^3$; $—C(O)R^5$; $—C(O)OR^7$ or $—C(O)NR^9R^{10}$;
$R^3$; $R^5$; $R^7$; $R^9$ and $R^{10}$ are each independently selected from H, substituted lower alkyl, lower alkyl, substituted aralkyl, aralkyl, substituted aryl or aryl.

Also disclosed herein is a method for detecting for the presence of $H_2S$ or $HS^-$ anion in a system, comprising contacting a sample from the system with a compound, or a protonate or salt thereof, having a structure represented by:

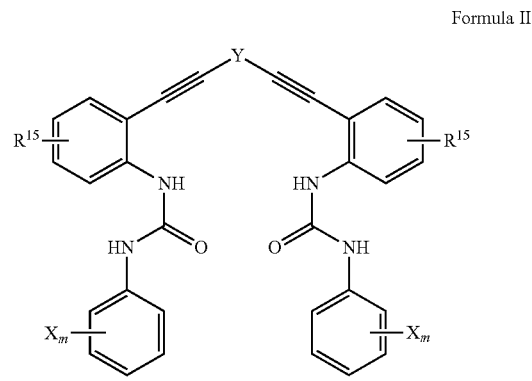

Formula II wherein Y represents a substituted aromatic group or an aromatic group;
each $R^{15}$ is independently H, alkyl, substituted alkyl, a polyether moiety, carboxyl, substituted carboxyl, carbamate, substituted carbonate, carbonyloxy, alkoxy, substituted alkoxy, haloalkyl, halogen, nitro, amino, amido, aryloxy, cyano, hydroxyl, or sulfonyl;
each X is independently halogen, alkoxy, substituted alkoxy, alkyl, substituted alkyl or a polyether moiety; and
m is 0 to 5.

Further disclosed herein is a method for detecting for the presence of $H_2S$ or an anionic sulfide species in a system, comprising contacting a sample from the system with a compound, or a protonate or salt thereof, having a structure that includes at least one moiety configured for reversible, non-covalent binding of the anionic sulfide species.

Also disclosed herein is a compound, or a protonate or salt thereof, having a structure represented by:

Formula II

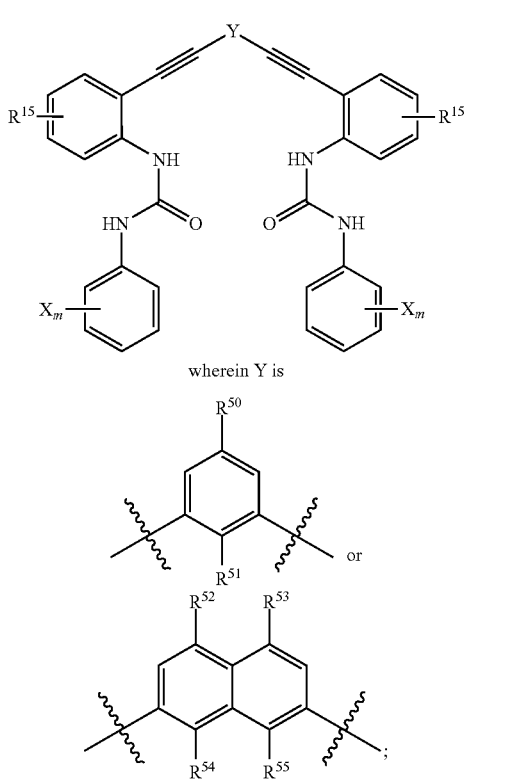

wherein Y is each $R^{15}$ is independently H, alkyl, substituted alkyl, a polyether moiety, carboxyl, substituted carboxyl, carbamate, substituted carbonate, carbonyloxy, alkoxy, substituted alkoxy, haloalkyl, halogen, nitro, amino, amido, aryloxy, cyano, hydroxyl, or sulfonyl;

each X is independently halogen, alkoxy, substituted alkoxy, alkyl, substituted alkyl or a polyether moiety; m is 0 to 5; and wherein $R^{50}$, $R^{51}$, $R^{52}$, $R^{53}$, $R^{54}$ and $R^{55}$ are each independently selected from hydrogen, alkyl, substituted alkyl, a polyether moiety, carboxyl, substituted carboxyl, carbamate, substituted carbonate, carbonyloxy, alkoxy, substituted alkoxy, haloalkyl, halogen, nitro, amino, aryloxy, cyano, hydroxyl, or sulfonyl.

The foregoing will become more apparent from the following detailed description, which proceeds with reference to the accompanying figures.

DETAILED DESCRIPTION

Figures 1A, 1B, 1C:
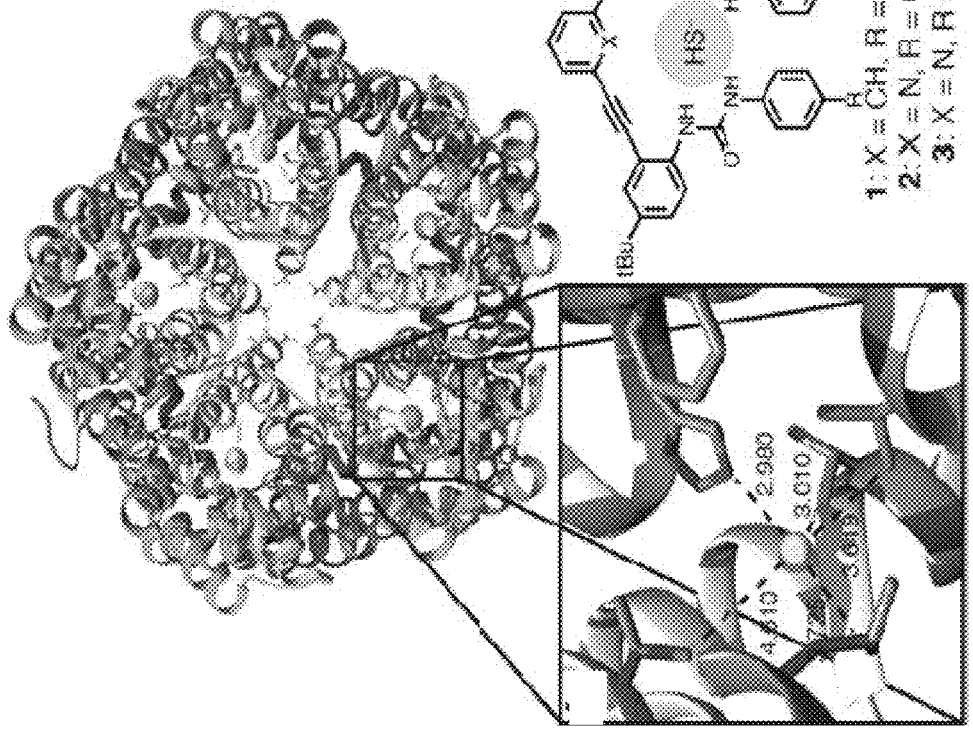
FIG. 1A. Complete protein structure of HSC (PDB: 3TDX) showing five individual channels. The bound anion is represented as a yellow sphere.
FIG. 1B. Enlargement of the binding pocket showing short contacts to His (2.980 Å), Thr (3.010 Å), Leu (3.725 Å) and Val (3.619 and 4.610 Å). External helices not involved in the highlighted short contacts are excluded for clarity.
FIG. 1C. Synthetic receptors 1-3.

Current tools for the detection of $HS^-$/$H_2S$ utilize non-reversible reaction based chemistry. Examples include nucleophilic attack by $HS^-$, reduction of an azide or nitro moiety, and metal coordination. The development of small molecule fluorescent probes that utilize supramolecular interactions will greatly expand the ability of researchers to investigate the role of hydrogen sulfide in biological systems without the disruption of endogenous concentrations of $H_2S$.

The receptor compounds and methods disclosed herein can be applied to biological fluorescent probes or sensors for $HS^-$/$H_2S$. The receptor compounds and methods disclosed herein can also be utilized for the storage, transport, and delivery of $HS^-$/$H_2S$ for possible therapeutic applications or scientific investigations.

A new method of detection for hydrosulfide anion ($HS^-$) and hydrogen sulfide ($H_2S$) is disclosed herein. This method utilizes reversible, supramolecular binding interactions which have not been previously reported. The supramolecular detection of $HS^-$/$H_2S$ is a novel strategy which allows for the detection of $HS^-$/$H_2S$ without disrupting or altering the analyte concentration during experimentation.

The receptors disclosed herein feature hydrogen bond donors to target the anionic portion of hydrosulfide and a hydrogen bond acceptor (or suitable pocket of electron density) to accommodate the very slightly acidic hydrogen atom. In particular, the receptors bind anions through tunable urea NH hydrogen bonds, and the central core incorporates an additional hydrogen bond donating arene (compounds 1, 4, 5 and 6 below) or a hydrogen bond accepting pyridine group (compounds 2 and 3 below).

In particular, disclosed herein is a series of bis(ethynylaniline) derivatives capable of binding hydrosulfide anion with association constants as high as 90,300±8700 $M^{-1}$, representing the first reversible binding of the hydrosulfide anion in a synthetic receptor. $^1H$ NMR and UV-Vis spectroscopy both indicate a greater selectivity for $HS^-$ in the pyridine core; however, the phenyl core shows a larger binding affinity, likely due to an additional hydrogen-bonding motif. The preference for the phenyl core highlights the unexpected conclusion that a C—H . . . S contact is favored over an N: . . . H—S contact by up to 0.9 kcal $mol^{-1}$. CH hydrogen bond donors are important components in targeting hydrosulfide reversibly, and receptors featuring appropriately polarized CH donors should exhibit enhanced selectivity and stronger binding. The results disclosed herein support reversible binding of $HS^-$, rather than covalent modification or deprotonation. The basic science of synthetic non-covalent binding of sulfide will help to identify new target proteins for the binding of sulfide, while also informing detection strategies that do not rely on irreversible covalent modification of fluorescent platforms for sulfide detection.

Compounds 1-6 (see below) have been shown to reversibly bind HS⁻ using hydrogen bonds. Compound 1 and 4-5 utilize four urea NH donors and one aryl CH donor. Compounds 2-3 utilize four urea NH donors and the free pyridine electrons as a hydrogen bond acceptor. Both strategies have proven to be viable platforms for HS⁻ detection. Compound 6 utilizes four NH donors and two aryl CH donors.

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

"Acyl" refers group of the formula RC(O)— wherein R is an organic group.

The term "aliphatic" includes alkyl, alkenyl, alkynyl, halogenated alkyl and cycloalkyl groups as described above. A "lower aliphatic" group is a branched or unbranched aliphatic group having from 1 to 10 carbon atoms.

The term "alkoxy" refers to a straight, branched or cyclic hydrocarbon configuration and combinations thereof, including from 1 to 20 carbon atoms, preferably from 1 to 10 carbon atoms, more preferably from 1 to 4 carbon atoms, that includes an oxygen atom at the point of attachment. An example of an "alkoxy group" is represented by the formula —OR, where R can be an alkyl group, optionally substituted with, e.g., an alkenyl, alkynyl, aryl, aralkyl, cycloalkyl, halogenated alkyl, or heterocycloalkyl group as described herein. Suitable alkoxy groups include methoxy, ethoxy, n-propoxy, i-propoxy, n-butoxy, i-butoxy, sec-butoxy, tert-butoxy cyclopropoxy, cyclohexyloxy, and the like.

The term "alkyl" refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 6 carbon atoms. Preferred alkyl groups have 1 to 4 carbon atoms. Alkyl groups may be "substituted alkyls" wherein one or more hydrogen atoms are substituted with a substituent such as halogen, cycloalkyl, alkoxy, amino, hydroxyl, aryl, alkenyl, or carboxyl. For example, a lower alkyl or ($C_1$-$C_6$)alkyl can be methyl, ethyl, propyl, isopropyl, butyl, iso-butyl, sec-butyl, pentyl, 3-pentyl, or hexyl; ($C_3$-$C_6$)cycloalkyl can be cyclopropyl, cyclobutyl, cyclopentyl, or cyclohexyl; ($C_3$-$C_6$)cycloalkyl($C_1$-$C_6$)alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; ($C_1$-$C_6$)alkoxy can be methoxy, ethoxy, propoxy, isopropoxy, butoxy, isobutoxy, sec-butoxy, pentoxy, 3-pentoxy, or hexyloxy; ($C_2$-$C_6$)alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; ($C_2$-$C_6$)alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; ($C_1$-$C_6$) alkanoyl can be acetyl, propanoyl or butanoyl; halo($C_1$-$C_6$) alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy($C_1$-$C_6$)alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; ($C_1$-$C_6$)alkoxycarbonyl can be methoxycarbonyl, ethoxycarbonyl, propoxycarbonyl, isopropoxycarbonyl, butoxycarbonyl, pentoxycarbonyl, or hexyloxycarbonyl; ($C_1$-$C_6$)alkylthio can be methylthio, ethylthio, propylthio, isopropylthio, butylthio, isobutylthio, pentylthio, or hexylthio; ($C_2$-$C_6$) alkanoyloxy can be acetoxy, propanoyloxy, butanoyloxy, isobutanoyloxy, pentanoyloxy, or hexanoyloxy.

The term "amine" or "amino" refers to a group of the formula —NRR', where R and R' can be, independently, hydrogen or an alkyl, alkenyl, alkynyl, aryl, aralkyl, cycloalkyl, halogenated alkyl, or heterocycloalkyl group described above.

The term "amide" refers to the formula —C(O)NRR', wherein R and R' independently can be a hydrogen, alkyl, alkenyl, alkynyl, aryl, aralkyl, cycloalkyl, halogenated alkyl, or heterocycloalkyl group described above.

The term "aralkyl" refers to an alkyl group that is substituted with one or more aryl groups (described below). A particular example of an aralkyl group is a benzyl group.

The term "aryl" refers to any carbon-based aromatic group including, but not limited to, phenyl, naphthyl, etc. The term "aromatic" also includes "heteroaryl groups," which are defined as aromatic groups that have at least one heteroatom incorporated within the ring of the aromatic group. Examples of heteroatoms include, but are not limited to, nitrogen, oxygen, sulfur, and phosphorous. The aryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl group can be unsubstituted.

"Carbonyl" refers to a radical of the formula —C(O)—. Carbonyl-containing groups include any substituent containing a carbon-oxygen double bond (C=O), including acyl groups, amides, carboxy groups, esters, ureas, carbamates, carbonates and ketones and aldehydes, such as substituents based on —COR or —RCHO where R is an aliphatic, heteroaliphatic, alkyl, heteroalkyl, hydroxyl, or a secondary, tertiary, or quaternary amine. "Carbonyloxy" refers to a group of the —OC(O)R where R is an aliphatic (e.g., alkyl) or aromatic (e.g., aryl) group.

"Carbonate" refers to a group of the formula —OC(O)O—. "Substituted carbonate" refers to a group of the formula —OC(O)OR. Likewise, as used herein the term "carbamate" refers to a group of the formula —OC(O)N(R)—, wherein R is H, or an aliphatic group, such as a lower alkyl group or an aralkyl group.

"Carboxyl" refers to a —COOH radical. Substituted carboxyl refers to —COOR where R is aliphatic, heteroaliphatic, alkyl, heteroalkyl, or a carboxylic acid or ester.

"Optional" or "optionally" means that the subsequently described event or circumstance can but need not occur, and that the description includes instances where said event or circumstance occurs and instances where it does not. Optionally substituted groups, such as "substituted alkyl," refers to groups, such as an alkyl group, having from 1-5 substituents, typically from 1-3 substituents, selected from alkoxy, optionally substituted alkoxy, acyl, acylamino, acyloxy, amino, aminoacyl, aminoacyloxy, aryl, carboxyalkyl, optionally substituted cycloalkyl, optionally substituted cycloalkenyl, optionally substituted heteroaryl, optionally substituted heterocyclyl, hydroxy, thiol and thioalkoxy.

The term "phosphoryl" refers to moieties of the formula —P(O)OR—, wherein R may be H, an aliphatic or aromatic moiety, a cation or a lone pair of electrons. Phosphoryl moieties may be further substituted to form phosphoramidates, phosphates and phosphonates.

The term "polyether moiety" may be an oligomer (which is inclusive of dimers and higher repeating units) or a polymer. Illustrative polyether moieties include those derived from an aliphatic polyether (e.g., paraformaldehyde, polyethylene glycol (PEG), polypropylene glycol, and polytetramethylene glycol, and those derived from an aromatic polyether (e.g., polyphenyl ether or poly(p-phenylene oxide)). A preferred polyether moiety is derived from PEG, also referred to herein as a poly(ethylene oxide). The PEG may be a straight chain PEG or a branched PEG. PEG is also inclusive of methoxypolyethylene glycol. In certain embodiments, the number of repeating ethylene oxide units in the PEG moiety may range from 2 to 50, more particularly from 2 to 10. The polyether moiety may be covalently bonded to the core motif via PEGylation procedures.

The term "sulfonyl" refers to the radical —SO$_2$—. The sulfonyl group can be further substituted with a variety of groups to form, for example, sulfonic acids, sulfonamides, sulfonate esters and sulfones.

Protected derivatives of the disclosed compound also are contemplated. A variety of suitable protecting groups for use with the disclosed compounds are disclosed in Greene and Wuts Protective Groups in Organic Synthesis; 3rd Ed.; John Wiley & Sons, New York, 1999.

It is understood that substituents and substitution patterns of the compounds described herein can be selected by one of ordinary skill in the art to provide compounds that are chemically stable and that can be readily synthesized by techniques known in the art and further by the methods set forth in this disclosure.

The structural formulas provided herein include salts of the illustrated compounds. Such salts can be formed when disclosed host compounds possess at least one basic group that can form acid-base salts with acids. Examples of basic groups present in exemplary disclosed host compounds include amino groups or imino groups. Examples of inorganic acids that can form salts with such basic groups include, but are not limited to, mineral acids such as hydrochloric acid, hydrobromic acid, sulfuric acid or phosphoric acid. Basic groups also can form salts with organic carboxylic acids, sulfonic acids, sulfo acids or phospho acids or N-substituted sulfamic acid, for example acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, and, in addition, with amino acids, for example with α-amino acids, and also with methanesulfonic acid, ethanesulfonic acid, 2-hydroxymethanesulfonic acid, ethane-1,2-disulfonic acid, benzenedisulfonic acid, 4-methylbenzenesulfonic acid, naphthalene-2-sulfonic acid, 2- or 3-phosphoglycerate, glucose-6-phosphate or N-cyclohexylsulfamic acid (with formation of the cyclamates) or with other acidic organic compounds, such as ascorbic acid.

Similarly, salts can be formed when disclosed host compounds possess at least one acidic group that can form acid-base salts with bases. Examples of acidic groups present in exemplary disclosed host compounds include carboxylic acid moieties and sulfonamide groups. Compounds that include at least one acidic group can form an acid-base salts with an inorganic or organic base. Examples of salts formed from inorganic bases include salts of the presently disclosed compounds with alkali metals such as potassium and sodium, alkaline earth metals, including calcium and magnesium and the like. Similarly, salts of acidic compounds with an organic base, such as an amine (as used herein terms that refer to amines should be understood to include their conjugate acids unless the context clearly indicates that the free amine is intended) are contemplated, including salts formed with basic amino acids, aliphatic amines, heterocyclic amines, aromatic amines, pyridines, guanidines and amidines. In addition, quaternary ammonium counterions also can be used.

Additionally, the structural formulas herein are intended to cover, where applicable, solvated as well as unsolvated forms of the compounds. "Solvate" refers to a compound physically associated with one or more solvent molecules. This physical association involves varying degrees of ionic and covalent bonding, including by way of example covalent adducts and hydrogen bonded solvates. In certain instances the solvate will be capable of isolation, for example when one or more solvent molecules are incorporated in the crystal lattice of the crystalline solid. "Solvate" encompasses both solution-phase and isolable solvates. Representative solvates include ethanol associated compounds, methanol associated compounds, and the like. "Hydrate" is a solvate wherein the solvent molecule(s) is/are H$_2$O. Solvate complexes may be described in shorthand form for example as (1·H$_2$O)$_2$, which refers to a hydrate, more specifically a 2+2 complex of compound 1 with water.

Compounds disclosed herein can be crystallized and can be provided in a single crystalline form or as a combination of different crystal polymorphs. As such, the compounds can be provided in one or more physical form, such as different crystal forms, crystalline, liquid crystalline or non-crystalline (amorphous) forms. Such different physical forms of the compounds can be prepared using, for example different solvents or different mixtures of solvents for recrystallization. Alternatively or additionally, different polymorphs can be prepared, for example, by performing recrystallizations at different temperatures and/or by altering cooling rates during recrystallization. The presence of polymorphs can be determined by X-ray crystallography, or in some cases by another spectroscopic technique, such as solid phase NMR spectroscopy, IR spectroscopy, or by differential scanning calorimetry.

In one embodiment the receptor compounds and salts thereof have the formula

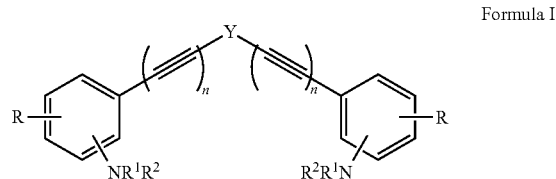

Formula I wherein Y represents an aromatic group or a substituted aromatic group;
n is 1 or 2;
R is independently H, alkyl, substituted alkyl, a polyether moiety, carboxyl, substituted carboxyl, carbamate, substituted carbonate, carbonyloxy, alkoxy, substituted alkoxy, haloalkyl, halogen, nitro, amino, amido, aryloxy, cyano, hydroxyl, or sulfonyl;
R$^1$ is H, substituted lower alkyl, lower alkyl, substituted aralkyl or aralkyl;
R$^2$ is selected from H, acyl, substituted aralkyl, aralkyl, phosphonyl, —SO$_2$R$^3$; —C(O)R$^5$; —C(O)OR$^7$ or —C(O)NR$^9$R$^{10}$;

$R^3$; $R^5$; $R^7$; $R^9$ and $R^{10}$ are each independently selected from H, substituted lower alkyl, lower alkyl, substituted aralkyl, aralkyl, substituted aryl or aryl.

In a further embodiment the receptor compounds and salts thereof have the formula Formula II

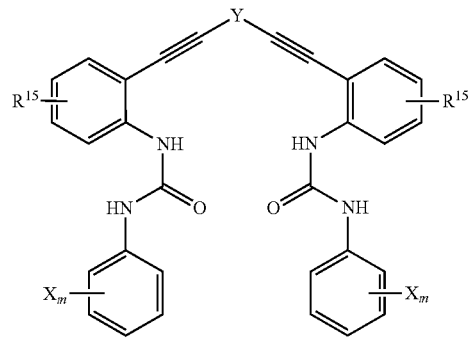

wherein Y represents a substituted aromatic group or an aromatic group;

each $R^{15}$ is independently H, alkyl, substituted alkyl, a polyether moiety, carboxyl, substituted carboxyl, carbamate, substituted carbonate, carbonyloxy, alkoxy, substituted alkoxy, haloalkyl, halogen, nitro, amino, amido, aryloxy, cyano, hydroxyl, or sulfonyl;

each X is independently halogen, alkoxy, substituted alkoxy, alkyl, substituted alkyl or a polyether moiety; and m is 0 to 5.

In certain embodiment of formula I or II, Y is:

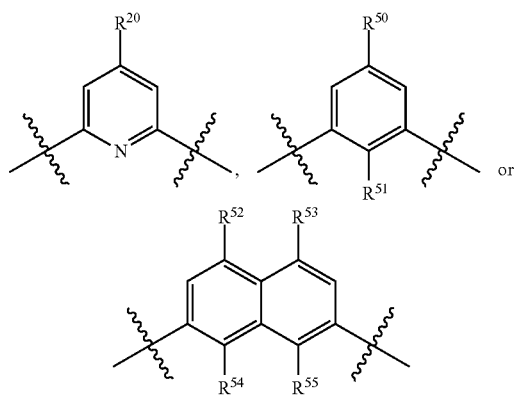

wherein $R^{20}$, $R^{50}$, $R^{51}$, $R^{52}$, $R^{53}$, $R^{54}$ and $R^{55}$ are each independently selected from hydrogen, alkyl, substituted alkyl, a polyether moiety, carboxyl, substituted carboxyl, carbamate, substituted carbonate, carbonyloxy, alkoxy, substituted alkoxy, haloalkyl, halogen, nitro, amino, aryloxy, cyano, hydroxyl, or sulfonyl.

In certain embodiments, $R^{51}$ is halogen.

In certain embodiments, $R^{20}$ is hydrogen, lower alkyl, nitro, amino, or lower alkoxy.

In certain embodiments, $R^{52}$, $R^{53}$, $R^{54}$ and $R^{55}$ are each hydrogen.

Alternative Y groups can be selected from

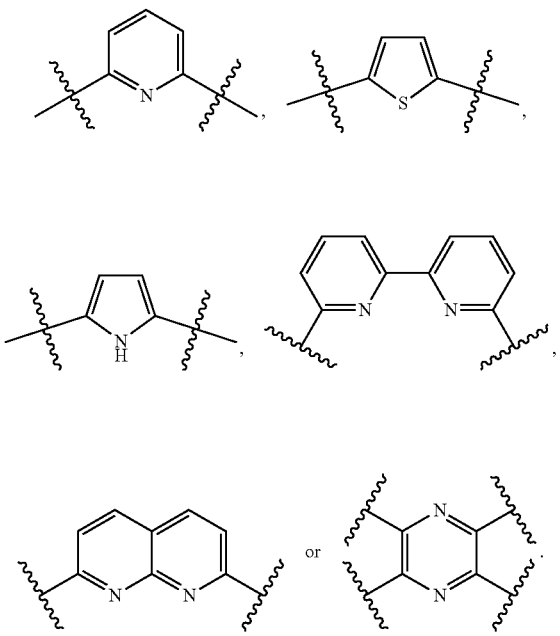 [SMILES: *c1cccc(*)n1 ; *c1ccc(*)s1 ; *c1ccc(*)[nH]1 ; *c1cccc(-c2cccc(*)n2)n1 ; *c1ccc2ccc(*)nc2n1 ; *c1nc(*)c(*)nc1*]

In certain embodiments of formula II, $R^{15}$ is lower alkyl, particularly tert-butyl.

In certain embodiments of formula II, there are two $R^{15}$ groups, each in a para position relative to the position of the —NH— group.

In certain embodiments of formula II, X is lower alkoxy, particularly methoxy.

In certain embodiments of formula II, m is 1 and the X group is in a para position relative to the position of the —NH— group.

Illustrative receptor compounds include:

1

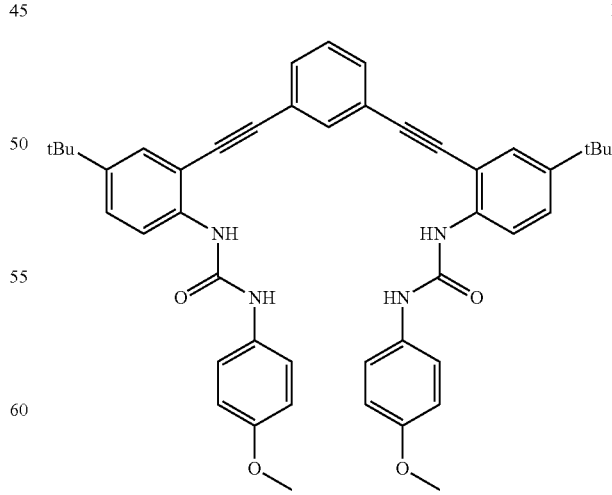

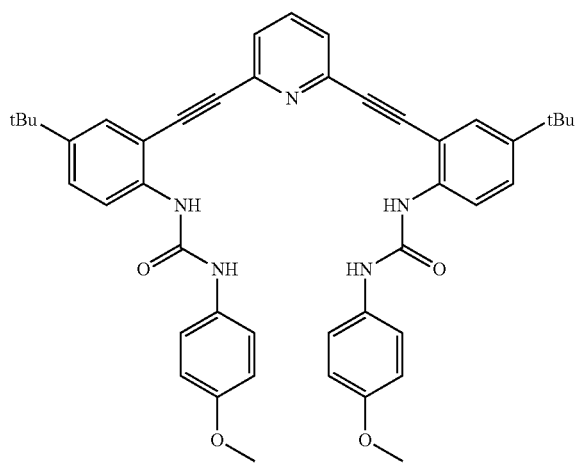

2

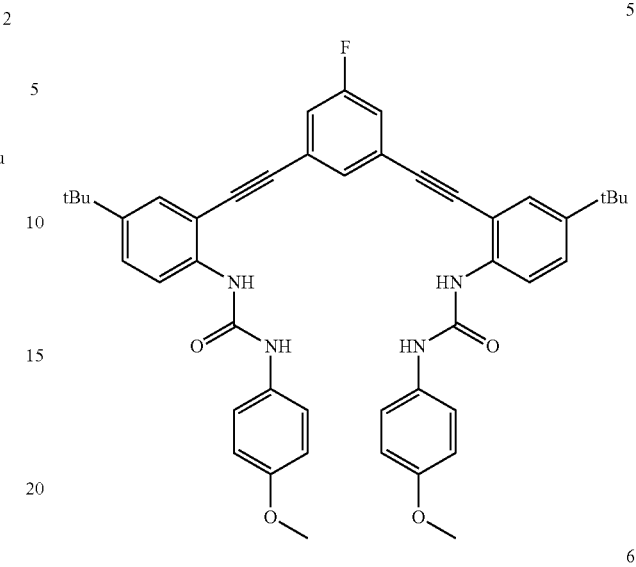

5

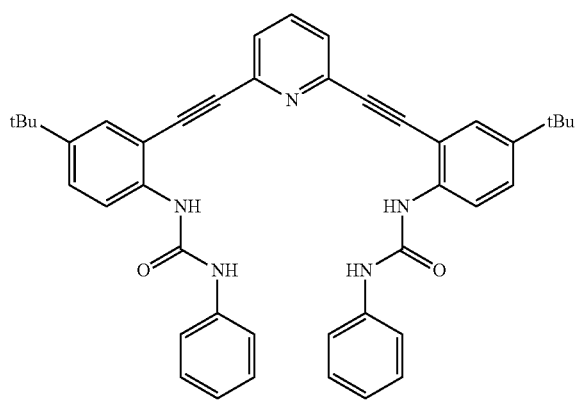

3

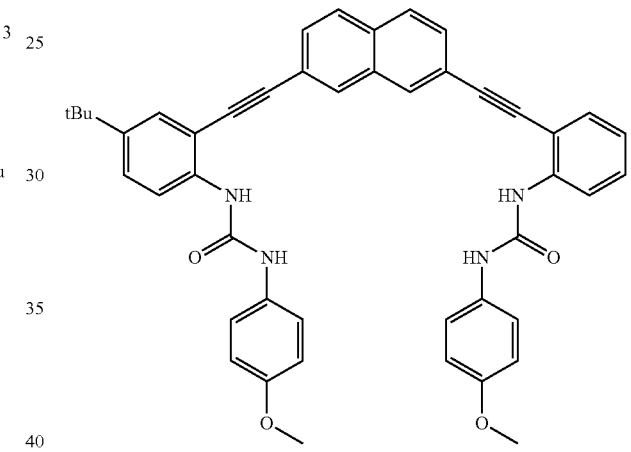

6

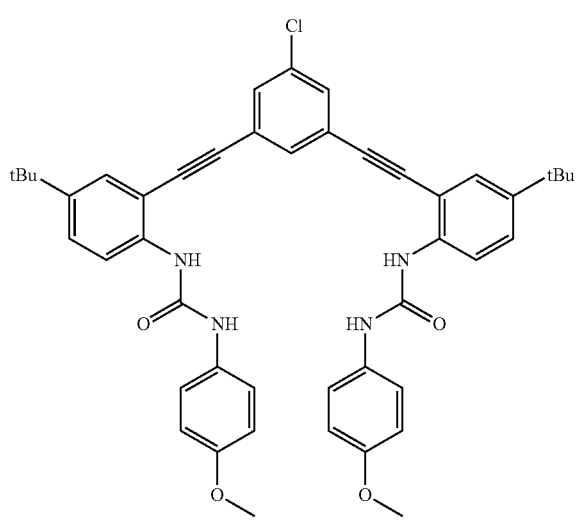

4

These compounds can be synthesized as described, for example, in U.S. Pat. Nos. 7,803,946 and 8,841,360 and U.S. Patent Publ. 2015-0355153-A1.

Exemplary receptor compounds exhibit ligand binding selectivity or recognition. The host compounds may exhibit selectivity in binding of HS⁻ or $H_2S$ or reporting of HS⁻ or $H_2S$'s presence. For example, a spectral property of a host compound, such as fluorescence, may shift upon binding certain ligands, but not others. It has been demonstrated for exemplary compounds disclosed herein that the spectral properties, such as the UV-Vis spectra shift noticeably upon binding of different guests. For example, the extended conjugation inherent in 2,6-bis(2-anilinoethynyl)pyridines derivatives produces distinct emission properties that will be used to monitor interactions with guest molecules.

In certain embodiments, the receptor compound may be included within a membrane of an electronic device (e.g., field effect transistor, ion-selective electrode, microfluidic, electrochemical cell, pre-concentration membrane, lab-on-a-chip membrane/component, etc.) to provide an electrical readout of the detection of $H_2S$ or HS⁻.

Figure 5:
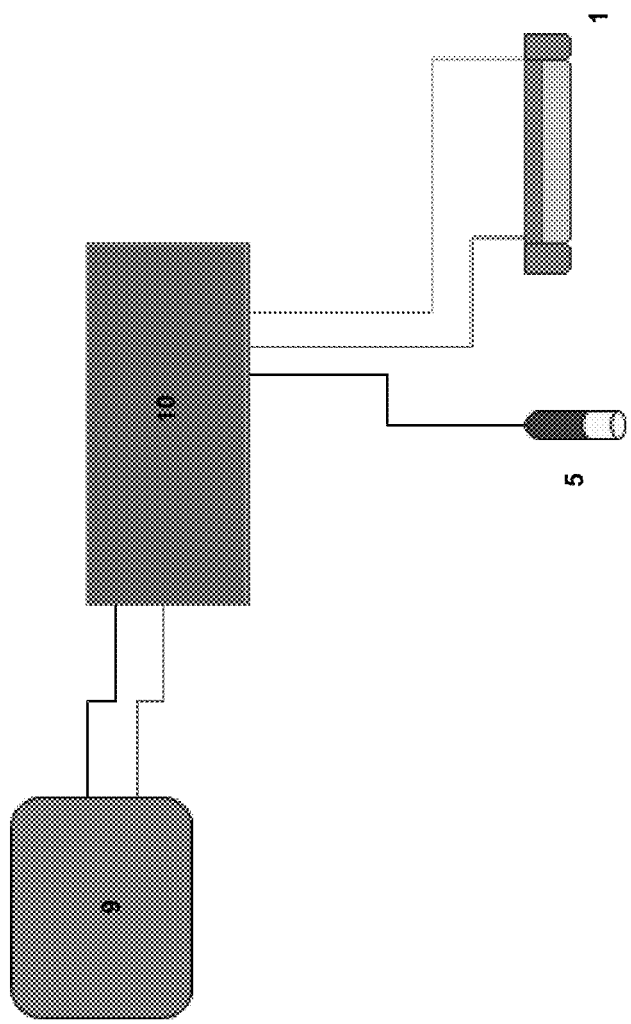
FIG. 5 is a schematic of a chemical sensing system.
Figure 6:
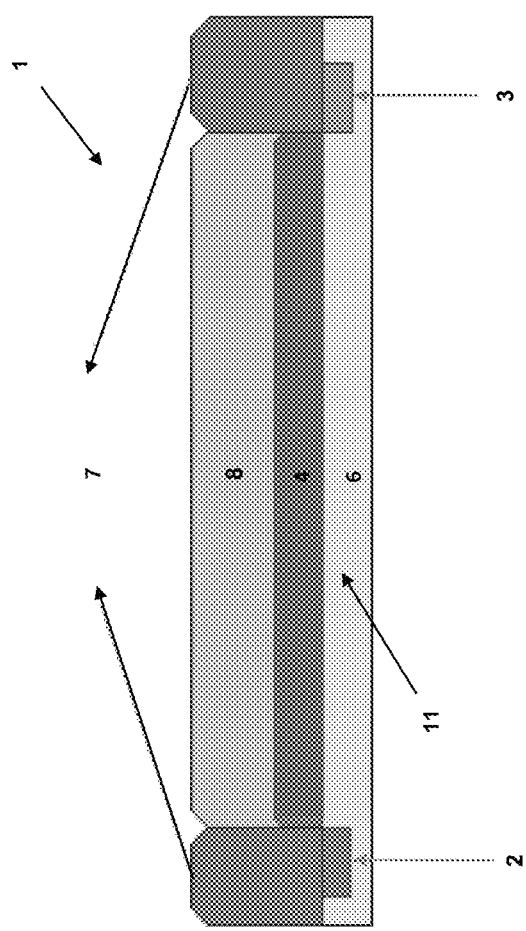
FIG. 6 is a cross-section of an illustrative embodiment of a chemical sensor disclosed herein.

In one embodiment, the receptor compound is included in a field effect transistor (FET) device. An illustrative FET device 1 is shown in FIGS. 5 and 6. When FETs are used as chemical sensors, they are usually called ChemFETs or ISFETs. An example FET is shown having the following five components: a source 2, a drain 3, a gate 4, a gate electrode 5, and bulk (or body) 6. The source 2 contacts a first portion of the bulk 6, and the drain 3 contacts a second portion of the bulk 6 that is locally distinct from the first portion. A region 11 of the bulk separates the source 2 from the drain 3. Gate 4 is disposed on a surface of the bulk 6 in a position between the source 2 and drain 3. When a ChemFET or ISFET (or almost any FET-based sensor) is made, the gate electrode 5 is separated in space from the gate 4. The gate electrode 5 becomes the reference electrode and in this configuration, those terms can be used interchangeably. The gate 4 and gate electrode 5 are the only components exposed to the sample environment. The source 2, drain 3, and bulk 6 are encapsulated or sealed off such as with an encapsulating polymer or $SiO_2$ 7.

A polymeric element 8 is disposed on a surface of the gate 4 that opposes the gate/bulk interface. The polymeric element 8 may be a polymer-containing coating or layer. In other words, the gate 4 is located between the polymeric element 8 and the bulk 6. The polymeric element 8 residing on the gate 4 (not on the gate electrode 5) determines the sensitivity and selectivity of the device. In general, the polymeric element 8 comprises at least three components. In certain embodiments, the polymeric element 8 consists of only a polymer, the receptor compound(s) disclosed herein, and an ionophore (i.e, a salt).

One component is the polymer itself which may be, but is not limited to, a polyvinyl chloride, polyvinyl alcohol, polystyrene, butadiene copolymer, polysiloxane, epoxy acrylate, methacrylate, urethane acrylate, polyacrylamide, among many others. In general, a suitable polymer must have the following characteristics:
1) Good adhesion to the gate substrate (which is typically silicon oxide or silicon nitride).
2) Good chemical resistance to other components and to common species present in the environment of intended use. For example, a device designed to detect hydrosulfide in water will require a polymer that is inert to hydrosulfide and water.
3) Sufficient mechanical strength.
4) Permeability to the target analyte.

Processing requirements are also considered. Polymers may be processed by solvent casting or by polymerization directly on the device such as by photopolymerization of acrylates. Many classes of polymers listed above require additives in order to achieve the required characteristics. For example, polyvinyl chloride must be highly plasticized (a large amount of plasticizer must be added) in order for the material to meet the requirements of the application. This is generally considered to be undesirable but it is often unavoidable.

The second component is the receptor compound(s) disclosed herein.

The third component is an ionophore that may be, but is not limited to, a salt such as tetraoctylammonium bromide which serves to make the polymer coating more ionic and, thus, more hospitable to water and water-soluble species like hydrosulfide. Salts typically have one component ion of significance to the application and another which is required but incidental. For example, the tetraoctylammonium component of tetraoctylammonium bromide, serves as a cationic feature of the material while the bromide is believed to exchange with other anions in the sample medium and is not considered an important part of the detection system. Tetraoctylammonium chloride works just as well. The primary characteristics of the salt are that the primary component be effectively immobile in the polymer coating. Viewed another way, the salt component should much more soluble in the polymer than it is in water, where the device is intended to function in water. The salts also have to be inert to the other polymer components as well as to the target analyte and sample environment.

When the polymer coating needs to be made cationic, as is the case with hydrosulfide detection, tetralkylammonium salts such as tetraoctylammonium or tetradodecylammonium are suitable. Lipophilic ions are usually used since it is almost always the case that the polymer is more lipophilic than the sample medium. This is the case with any aqueous application of these devices.

The polymer itself accounts for most of the mass of the polymer coating and the other components are incorporated at various ratios. The receptor is typically present in an amount of 0.1 to 5%, more particularly 0.1 to 1% by weight, based on the total weight of the polymer coating. The salts are typically incorporated at 1% to 5% by weight, based on the total weight of the polymer coating. The polymer itself along with any required polymer additives (plasticizers, for example) makes up the remainder of the polymer coating.

A data logger or data collection device 9 is coupled to a control circuit 10. The data collection device 9 may be any device used to interpret and record an analog voltage.

Illustrative devices include Fluke RMS multimeters, National Instruments DAQ devices, and other analog-to-digital conversion instruments.

The control circuit 10, also called the interface circuit, is associated with each individual chemical sensor 1 and is required to obtain a measurement signal from the chemical sensor. There are many possible configurations and operational modes for control circuits. An illustrative control circuit is known as "Voltage Feedback to the Reference Electrode." In short, this operates by maintaining constant voltage and from source to drain (source and drain are features of the chemical sensor, when that sensor is a FET device) as well as a constant drain current while allowing the reference electrode voltage to float. This voltage at the reference electrode is taken as the measurement signal and relates linearly to the log of the concentration of the target species (hydrosulfide in this case).

The reference electrode 5, when the chemical sensor is a FET device, is the gate electrode. There are multiple options for reference electrode material and form factor, including, for example, gold pins and Ag/AgCl reference electrodes.

The reference electrode and chemical sensor are immersed in an aqueous solution containing the analyte of interest (e.g., hydrosulfide). Then the control circuit is powered and, when the output voltage is stable, the voltage is taken as the measurement signal. Stable voltage is typically achieved within one minute. In some cases, higher voltage corresponds to higher concentrations of the target analyte, although the relationship can be reversed.

Illustrative embodiments of the methods and materials disclosed herein are described in the numbered clauses below:

1. A method for detecting for the presence of $H_2S$ or an anionic sulfide species in a system, comprising contacting a sample from the system with a compound, or a protonate or salt thereof, having a structure represented by:

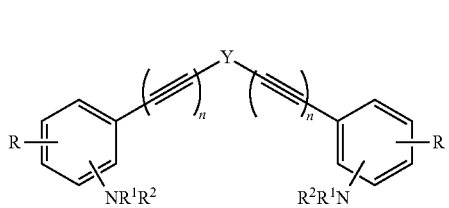

Formula I wherein Y represents an aromatic group or a substituted aromatic group;
n is 1 or 2;
R is independently H, alkyl, substituted alkyl, a polyether moiety, carboxyl, substituted carboxyl, carbamate, substituted carbonate, carbonyloxy, alkoxy, substituted alkoxy, haloalkyl, halogen, nitro, amino, amido, aryloxy, cyano, hydroxyl, or sulfonyl;
$R^1$ is H, substituted lower alkyl, lower alkyl, substituted aralkyl or aralkyl;
$R^2$ is selected from H, acyl, substituted aralkyl, aralkyl, phosphonyl, —$SO_2R^3$; —$C(O)R^5$; —$C(O)OR^7$ or —$C(O)NR^9R^{10}$;
$R^3$; $R^1$; $R^7$; $R^9$ and $R^{10}$ are each independently selected from H, substituted lower alkyl, lower alkyl, substituted aralkyl, aralkyl, substituted aryl or aryl.

2. A method for detecting for the presence of $H_2S$ or an anionic sulfide species in a system, comprising contacting a sample from the system with a compound, or a protonate or salt thereof, having a structure represented by:

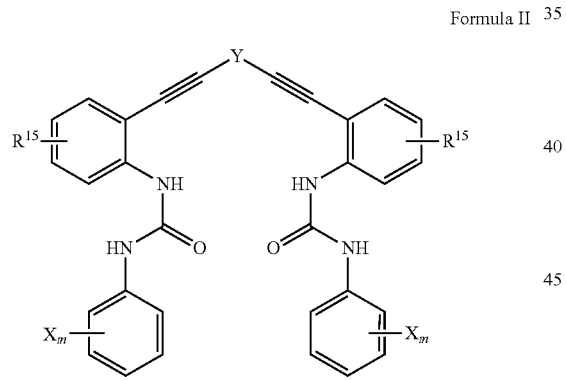

Formula II wherein Y represents a substituted aromatic group or an aromatic group;
each $R^{15}$ is independently H, alkyl, substituted alkyl, a polyether moiety, carboxyl, substituted carboxyl, carbamate, substituted carbonate, carbonyloxy, alkoxy, substituted alkoxy, haloalkyl, halogen, nitro, amino, amido, aryloxy, cyano, hydroxyl, or sulfonyl;
each X is independently halogen, alkoxy, substituted alkoxy, alkyl, substituted alkyl or a polyether moiety; and
m is 0 to 5.

3. The method of clause 1 or 2, wherein the system comprises an aqueous system.
4. The method of clause 1 or 2, wherein the system comprises a biological system.
5. The method of any one of clauses 1 to 4, wherein Y is selected from:

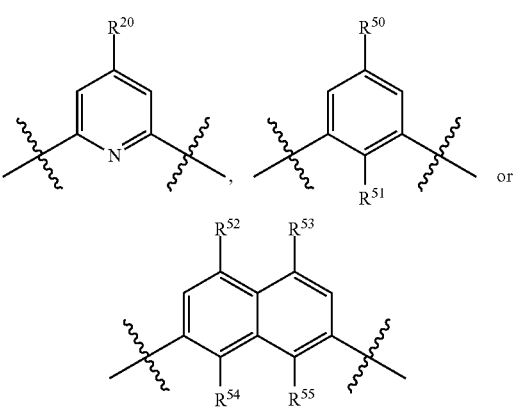

wherein $R^{20}$, $R^{50}$, $R^{51}$, $R^{52}$, $R^3$, $R^4$ and $R^{55}$ are each independently selected from hydrogen, alkyl, substituted alkyl, a polyether moiety, carboxyl, substituted carboxyl, carbamate, substituted carbonate, carbonyloxy, alkoxy, substituted alkoxy, haloalkyl, halogen, nitro, amino, aryloxy, cyano, hydroxyl, or sulfonyl.

6. The method of clause 5, wherein Y is

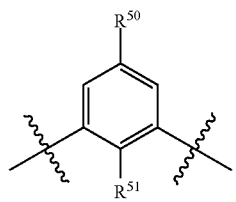

wherein $R^{50}$ is halogen.

7. The method of clause 5, wherein Y is

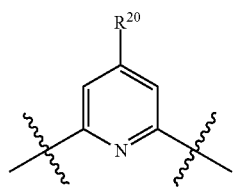

wherein $R^{20}$ is hydrogen.

8. A method for detecting for the presence of $H_2S$ or an anionic sulfide species in a system, comprising contacting a sample from the system with a compound, or a protonate or salt thereof, having a structure that includes at least one moiety configured for reversible, non-covalent binding of the anionic sulfide species.
9. The method of clause 8, wherein the reversible, non-covalent bonding involves hydrogen bonding.
10. The method of clause 9, wherein the hydrogen bonding includes a C—H . . . S hydrogen bond.
11. The method of clause 8, wherein the at least one moiety is a CH hydrogen bond donor.
12. A compound, or a protonate or salt thereof, having a structure represented by:

Formula II

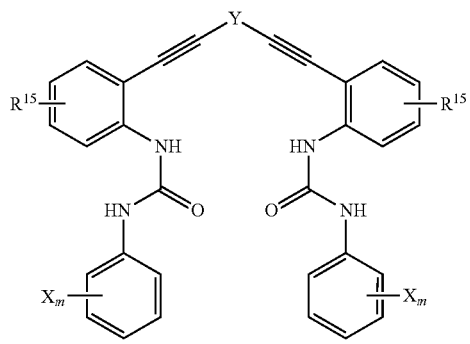

wherein Y is

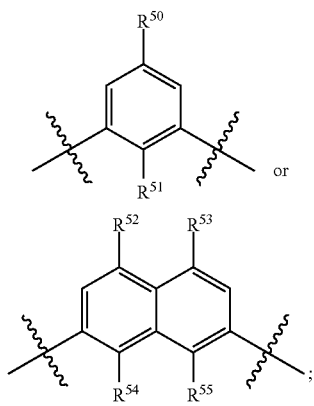

each $R^{15}$ is independently H, alkyl, substituted alkyl, a polyether moiety, carboxyl, substituted carboxyl, carbamate, substituted carbonate, carbonyloxy, alkoxy, substituted alkoxy, haloalkyl, halogen, nitro, amino, amido, aryloxy, cyano, hydroxyl, or sulfonyl;

each X is independently halogen, alkoxy, substituted alkoxy, alkyl, substituted alkyl or a polyether moiety;

m is 0 to 5; and wherein $R^{50}$, $R^{51}$, $R^{52}$, $R^{53}$, $R^{54}$ and $R^{55}$ are each independently selected from hydrogen, alkyl, substituted alkyl, a polyether moiety, carboxyl, substituted carboxyl, carbamate, substituted carbonate, carbonyloxy, alkoxy, substituted alkoxy, haloalkyl, halogen, nitro, amino, aryloxy, cyano, hydroxyl, or sulfonyl.

13. The compound of clause 12, wherein Y is

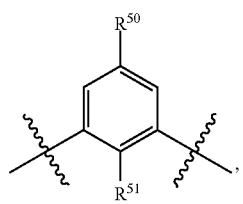

and $R^{50}$ is halogen and $R^{51}$ is hydrogen.

14. The compound of clause 12, wherein Y is

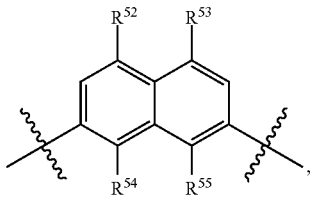

and $R^{52}$, $R^{53}$, $R^{54}$ and $R^{55}$ are each hydrogen.

15. The compound of any one of clauses 12 to 14, wherein each $R^{15}$ is alkyl; m is 1, and X is alkoxy.

EXAMPLES

Figure 2A:
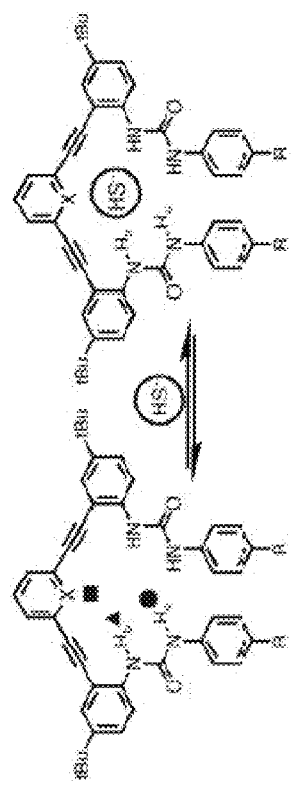
FIG. 2A. Scheme showing $HS^-$ host-guest equilibrium.
Figure 2B:
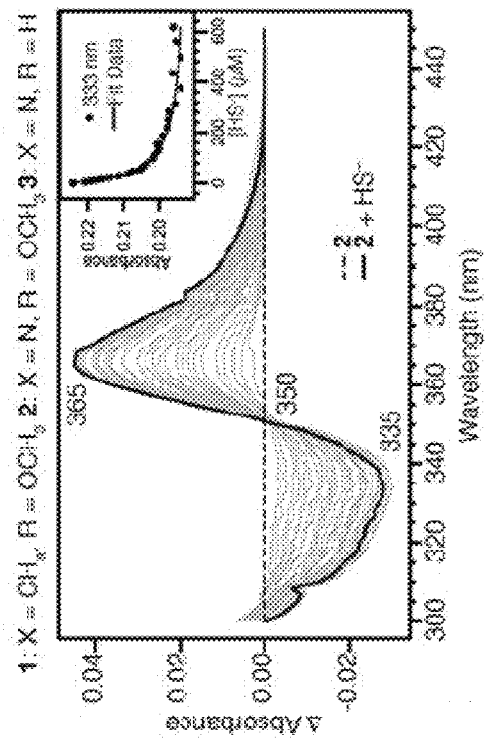
FIG. 2B. Representative UV-Vis difference titration of $NBu_4SH$ with 10 μM 2 in MeCN and fit to a 1:1 binding isotherm (inset).
Figure 2C:
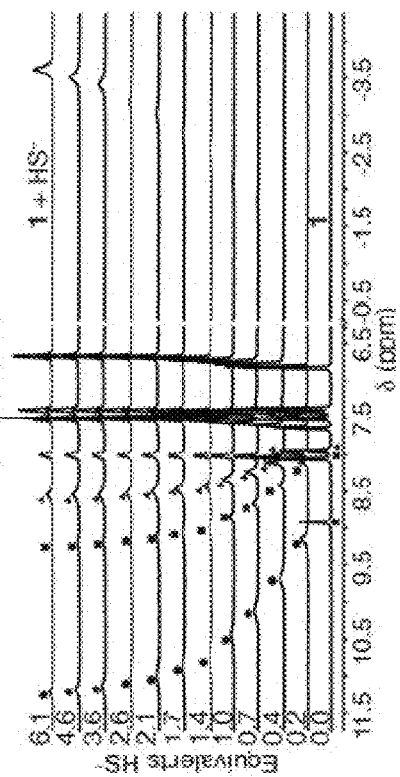
FIG. 2C. 1H NMR spectra of a titration of 0.988 mM 1 with $NBu_4SH$ in 10% MSOd6/CD3CN.

To investigate whether $HS^-$ is a suitable anionic guest for compounds 1-3, we titrated $NBu_4SH$ into 0.5-1.0 mM solution of each host in 10% $DMSO-d_6/CD_3CN$ and monitored the titrations by $^1H$ NMR spectroscopy. In each case, we observed that the urea NH resonances shifted significantly downfield upon $HS^-$ addition, consistent with anion binding (FIG. 2). For example, upon addition of $HS^-$ to a 0.988 mM solution of 1, the aryl $CH_a$ shifted from 7.99 to 9.24 ppm, and the $NH_b$ and $NH_c$ urea protons shift downfield from 7.94 and 8.92 to 8.63 and 11.18 ppm, respectively. Highlighting the preference of 1-3 for $HS^-$ rather than $H_2S$, addition of $H_2S$ gas to any of the receptors failed to change the UV-Vis or NMR spectra of the hosts. We also confirmed that the observed changes in the NMR spectra upon $HS^-$ addition were not merely due to deprotonation of the urea NH groups. Addition of the strong base 1,8-diazabicyclo[5.4.0]undec-7-ene (DBU) produced significantly different UV-Vis and NMR spectra than those observed upon $HS^-$ addition. On the basis of the high nucleophilicity of $HS^-$, we also wanted to confirm that the anion did not irreversibly modify the alkyne moieties of the host scaffolds. Monitoring the $^{13}C\{^1H\}$ NMR spectrum of a 2.3 mM solution of 1 before and after addition of 10 equivalents of $HS^-$ confirmed that the alkynes were unreactive toward $HS^-$. Titration data of $HS^-$ with the host fit to simple 1:1 binding isotherm models, and a new, upfield-shifted peak appears for bound hydrosulfide. Taken together, these results support the hypothesis that $HS^-$ acts an anionic guest within the pocket of the host, rather than covalently modifying the host scaffold.

To determine whether receptors 1-3 exhibited selectivity for $HS^-$ over other similar anions, we performed comparison titrations with NBu4Cl under identical conditions. Using 1H NMR titration data, we established that pyridine-based hosts 2 and 3 overall had significantly lower binding constants for both anions than did phenyl core host 1. This difference is likely due to the extra CH hydrogen bond donated from the phenyl core; however, it does not meet our initial hypothesis that $HS^-$ should also act as a weak hydrogen bond donor to an acceptor (e.g., pyridine nitrogen) on the host receptor (2-3). Despite the lower binding affinities, the pyridine-based hosts 2 and 3 exhibited 6-fold selectivity for $HS^-$ over $Cl^-$, whereas host 1 exhibited 2.8-fold selectivity. The higher selectivity is likely due to the pyridine lone pair acting as a hydrogen bond acceptor, which provides an additional stabilizing interaction for $HS^-$ and a destabilizing interaction for $Cl^-$. The phenyl core of host 1 donates a hydrogen bond to both anionic guests, resulting in decreased selectivity for hydrosulfide, even if this CH hydrogen bond is an important component to the high overall binding energy.

To further investigate the difference in anion selectivity, binding constants were also measured at lower concentrations by UV-Vis spectroscopy in MeCN; the data are summarized in Table 1.

TABLE 1

HS⁻ and Cl⁻ Binding Parameters in Hosts 1-3.

| Host | Solvent | HS⁻ (log($K_a$)) ΔG (kcal mol⁻¹) | Cl⁻ (log($K_a$)) ΔG (kcal mol⁻¹) |
|---|---|---|---|
| 1 | 10% DMSO-$d_6$/CD$_3$CN | 3.70 ± 0.07[a] −5.05 | 3.25 ± 0.03[a] −4.43 |
|   | MeCN | 4.96 ± 0.04[b] −6.76 | 4.53 ± 0.07[b] −6.18 |
| 2 | 10% DMSO-$d_6$/CD$_3$CN | 3.04 ± 0.06[a] −4.15 | 2.34 ± 0.07[a] −3.19 |
|   | MeCN | 4.30 ± 0.07[b] −5.86 | 3.19 ± 0.07[b] −4.35 |
| 3 | 10% DMSO-$d_6$/CD$_3$CN | 3.12 ± 0.07[a] −4.25 | 2.34 ± 0.02[a] −3.19 |
|   | MeCN | 4.45 ± 0.07[b] −6.07 | 3.08 ± 0.06[b] −4.20 |

[a]Fitting NMR spectroscopy data.
[b]Fitting UV-Vis spectroscopy data.

We expected that removal of the DMSO co-solvent would increase the observed binding affinities since acetonitrile is a slightly less competitive solvent (especially as a hydrogen bond acceptor). Addition of NBu$_4$SH to a 10 μM solution of 1, 2, or 3 resulted in attenuation of the 330 nm absorbance with concomitant increase at 360 nm, while proceeding through a well-anchored isosbestic point near 350 nm. As expected, removal of the DMSO co-solvent produced significantly higher binding affinities, with host 1 having a binding constant of 90,300 M⁻¹ and hosts 2 and 3 providing binding constants of ~25,000 M¹. In the case of 1, the selectivity for HS¹ over Cl⁻ remained similar to the 10% DMSO-$d_6$/CD$_3$CN system, whereas in the case of the pyridine core, a significant increase in selectivity is observed (~18.5:1 HS⁻:Cl⁻). The increase in analyte selectivity is primarily due to changes in binding energy of the chloride host-guest system. The difference between the binding energy of HS⁻ with 1 and 2 is the same in both solvents (ΔΔG=0.90 kcal mol⁻¹). In contrast, the Cl⁻ binding energy difference is solvent dependent with a larger change in pure acetonitrile (ΔΔG=1.24 (DMSO/CH$_3$CN) vs. 1.83 (CH3CN) kcal mol⁻¹). In the case of HS⁻, the ΔΔG is the difference between two stabilizing hydrogen bond motifs and leads to an estimate that a C—H . . . S hydrogen bond is up to 0.90 kcal mol⁻¹ stronger than an S—H . . . N hydrogen bond. The ΔΔG of Cl⁻ binding is larger because this represents the difference between a small repulsive N: . . . Cl contact and an attractive C—H . . . Cl hydrogen bond.

Figures 3A, 3B, 3C, 3D:
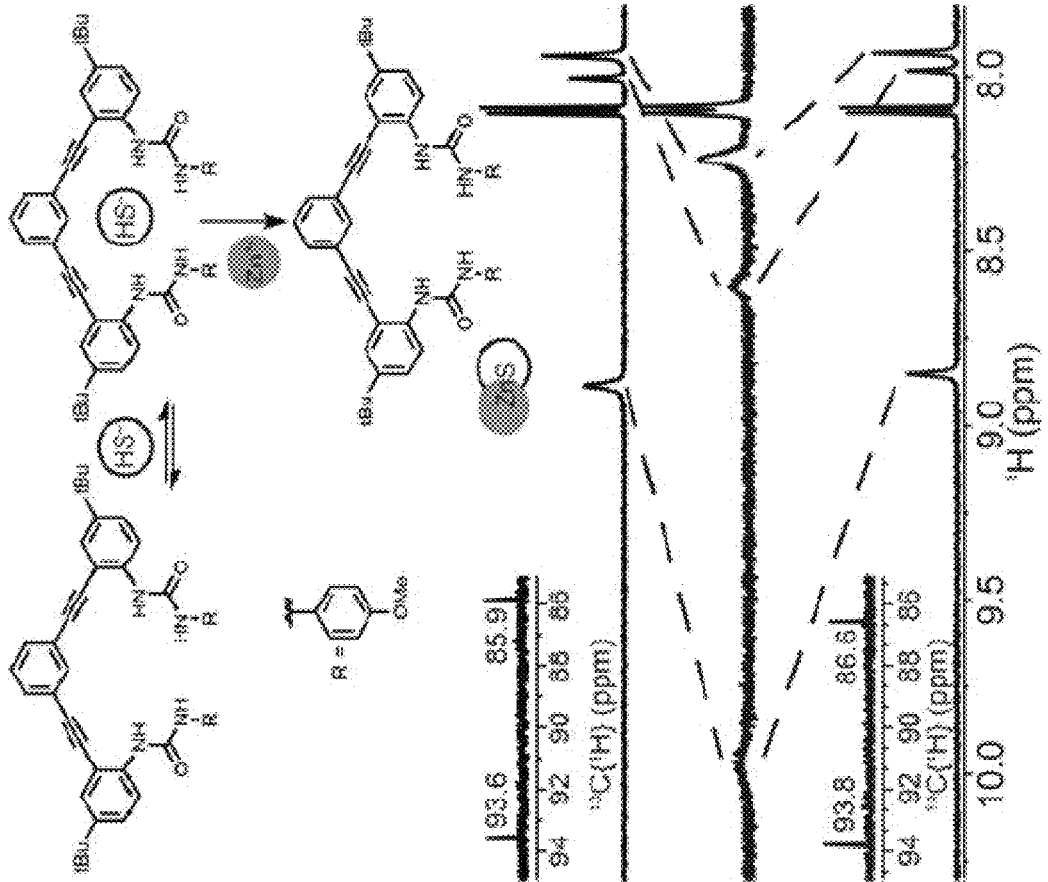
FIG. 3A. Reversibility reaction scheme.
FIG. 3B. 1H NMR spectrum of a 1.0 mM solution of 1 in 10% DMSO-$d_6$/$CD_3CN$.
FIG. 3C. Treatment with 2 equiv. of $NBu_4SH$.
FIG. 3D. Addition of 4 equiv. $Zn(OAc)_2$. Each inset shows the $^{13}C\{^1H\}$ resonances corresponding to the alkyne region of 1.

To further demonstrate the reversibility of HS⁻ binding, we treated a 1.0 mM solution of 1 in 10% DMSO-$d_6$/CD$_3$CN (FIG. 3a) with 2 equivalents of NBu$_4$SH to form the HS⁻ bound adduct (FIG. 3b), after which 4 equivalents of Zn(OAc)$_2$ were added. Addition of the Zn(II) salt rapidly resulted in precipitation of ZnS and regenerated the proton NMR spectrum corresponding to free 1 (FIG. 3c). Addition of 5 more equivalents of NBu$_4$SH at the end of the reaction regenerated the HS⁻ host-guest complex, confirming the reversibility of binding in this scaffold. Importantly, the $^{13}$C{$^1$H} resonances of the alkyne carbons did not shift significantly, confirming that there was no covalent modification of the receptor scaffold.

Figure 4:
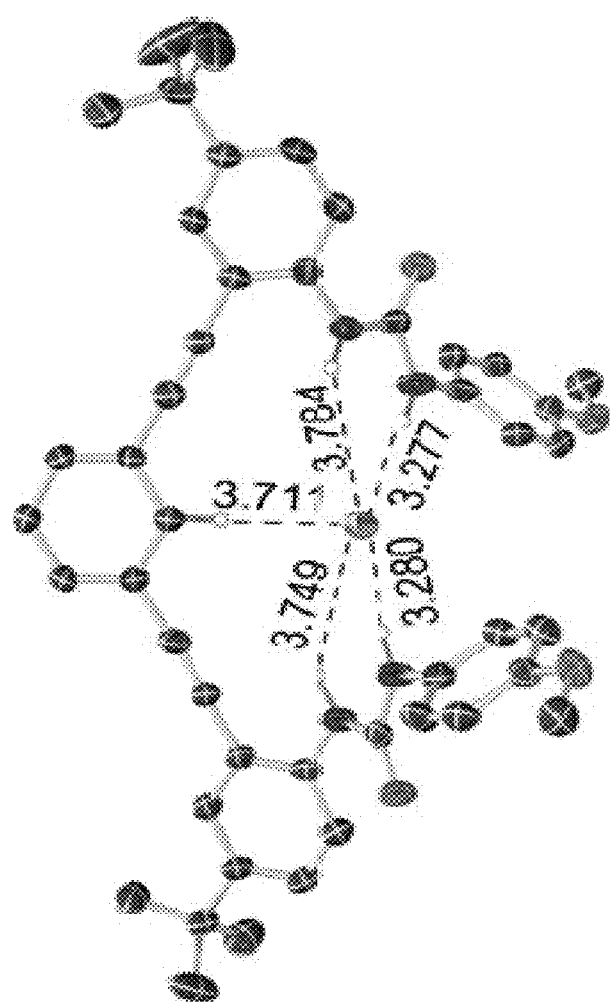
FIG. 4. ORTEP representation showing selected hydrogen bond distances. Hydrogens not interacting with the bound $HS^-$ are removed for clarity.

Single crystals of [1·HS⁻ ][NBu$_4$+] were grown by layering n-hexanes onto an equimolar solution of 1 and NBu$_4$SH in THF in a glovebox. [1·HS⁻ ][NBu$_4$+] crystallizes in the space group Pna21 with one molecule of THF per unit cell. Consistent with the solution NMR data, the HS⁻ occupies the binding pocket created by an aryl proton and four urea protons with the NBu$_4$⁺ cation sitting just above the sulfide-phenyl core plane. The structure shows five hydrogen bonds from the host to the bound sulfide guest. The C—H . . . S hydrogen bond (3.711 Å) is longer than those formed between the distal bis(urea) protons (3.277, 3.281 Å) (FIG. 4a). The average of all five hydrogen bond distances from the host to the guest is 3.56 Å, and all fall within previously defined criteria for hydrogen bonds. The host conformation in [1·HS⁻ ] is remarkably similar to the previously published chloride-bound structure, with an RMS distance between the two structures of only 0.184 Å. These data demonstrate the similar recognition geometries required for Cl⁻ and HS⁻ binding, again highlighting the potential for HS⁻ to be a potential substrate for classical Cl⁻ binding domains in both native and synthetic systems.

In view of the many possible embodiments to which the principles of the disclosed compositions and methods may be applied, it should be recognized that the illustrated embodiments are only preferred examples of the invention and should not be taken as limiting the scope of the invention.

What is claimed is:

1. A device comprising:
   a source;
   a drain;
   a gate;
   a bulk layer, wherein the source contacts a first portion of the bulk, and the drain contacts a second portion of the bulk that is physically distinct from the first portion and the gate is disposed on a surface of the bulk in a position between the source and the drain forming a gate/bulk interface; and
   a polymeric layer disposed on a surface of the gate that opposes the gate/bulk interface, wherein the polymeric layer comprises a (A) polymer and, incorporated within the polymeric layer,
   (B)(i) a compound, or a protonate or salt thereof, having a structure represented by:

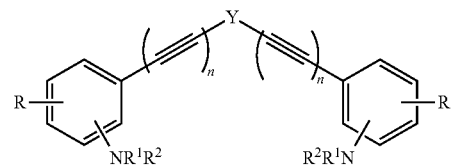

Formula I wherein Y represents an aromatic group or a substituted aromatic group;
n is 1 or 2;
R is independently H, alkyl, substituted alkyl, a polyether moiety, carboxyl, substituted carboxyl, carbamate, substituted carbonate, carbonyloxy, alkoxy, substituted alkoxy, haloalkyl, halogen, nitro, amino, amido, aryloxy, cyano, hydroxyl, or sulfonyl;
R¹ is H, substituted lower alkyl, lower alkyl, substituted aralkyl or aralkyl;
R² is selected from H, acyl, substituted aralkyl, aralkyl, phosphonyl, —SO$_2$R³; —C(O)R⁵; —C(O)OR⁷ or —C(O)NR⁹R¹⁰;

$R^3$; $R^5$; $R^7$; $R^9$ and $R^{10}$ are each independently selected from H, substituted lower alkyl, lower alkyl, substituted aralkyl, aralkyl, substituted aryl or aryl; or (B)(ii) a compound, or a protonate or salt thereof, having a structure represented by:

Formula II

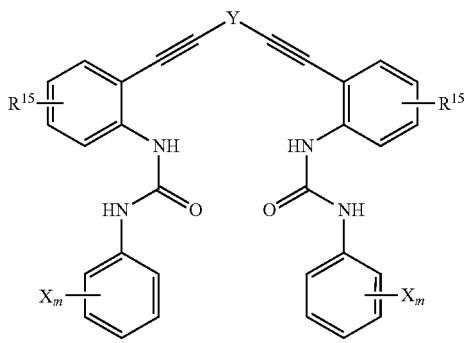

wherein Y represents a substituted aromatic group or an aromatic group;

each $R^{15}$ is independently H, alkyl, substituted alkyl, a polyether moiety, carboxyl, substituted carboxyl, carbamate, substituted carbonate, carbonyloxy, alkoxy, substituted alkoxy, haloalkyl, halogen, nitro, amino, amido, aryloxy, cyano, hydroxyl, or sulfonyl;

each X is independently halogen, alkoxy, substituted alkoxy, alkyl, substituted alkyl or a polyether moiety; and m is 0 to 5.

2. The device of claim 1, wherein Y is

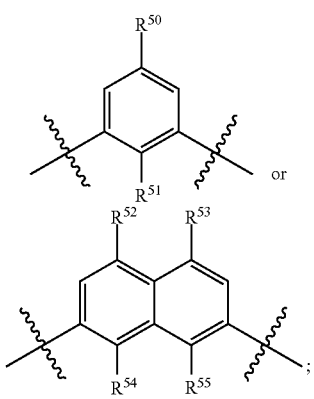

wherein $R^{50}$, $R^{51}$, $R^{52}$, $R^{53}$, $R^{54}$ and $R^{55}$ are each independently selected from hydrogen, alkyl, substituted alkyl, a polyether moiety, carboxyl, substituted carboxyl, carbamate, substituted carbonate, carbonyloxy, alkoxy, substituted alkoxy, haloalkyl, halogen, nitro, amino, aryloxy, cyano, hydroxyl, or sulfonyl.

3. The device of claim 1, wherein the polymer is selected from at least one of a polyvinyl chloride, polyvinyl alcohol, polystyrene, butadiene copolymer, polysiloxane, epoxy acrylate, methacrylate, urethane acrylate, polyacrylamide, or a combination thereof.

4. The device of claim 1, wherein the polymeric layer further incorporates at least one ionophore.

5. The device of claim 1, wherein the polymeric layer further incorporates at least one 5etraalkylammonium salt.

6. The device of claim 1, wherein (B)(i) or (B)(ii) is present in the polymeric layer in an amount of 0.1 to 5% by weight, based on the total weight of the polymeric element.

7. The device of claim 1, wherein (B)(i) is incorporated within the polymeric layer.

8. The device of claim 1, wherein (B)(ii) is incorporated within the polymeric layer.

9. A device comprising:
a source;
a drain;
a gate;
a bulk layer, wherein the source contacts a first portion of the bulk, and the drain contacts a second portion of the bulk that is physically distinct from the first portion and the gate is disposed on a surface of the bulk in a position between the source and the drain forming a gate/bulk interface; and
a polymeric element disposed on a surface of the gate that opposes the gate/bulk interface, wherein the polymeric element comprises a (A) polymer and (B)(i) a compound, or a protonate or salt thereof, having a structure represented by:

Formula I

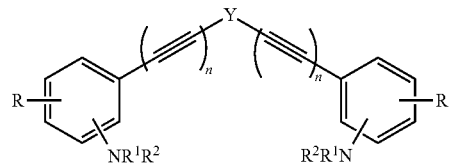

wherein Y is

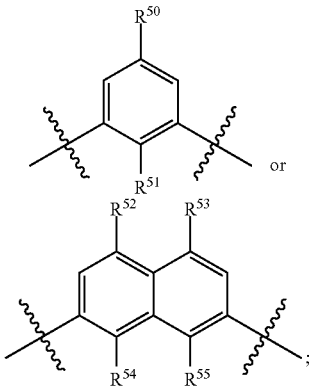

wherein $R^{50}$, $R^{51}$, $R^{52}$, $R^{53}$, $R^{54}$ and $R^{55}$ are each independently selected from hydrogen, alkyl, substituted alkyl, a polyether moiety, carboxyl, substituted carboxyl, carbamate, substituted carbonate, carbonyloxy, alkoxy, substituted alkoxy, haloalkyl, halogen, nitro, amino, aryloxy, cyano, hydroxyl, or sulfonyl;

n is 1 or 2;

R is independently H, alkyl, substituted alkyl, a polyether moiety, carboxyl, substituted carboxyl, carbamate, substituted carbonate, carbonyloxy, alkoxy, substituted alkoxy, haloalkyl, halogen, nitro, amino, amido, aryloxy, cyano, hydroxyl, or sulfonyl;

R¹ is H, substituted lower alkyl, lower alkyl, substituted aralkyl or aralkyl;

R² is selected from H, acyl, substituted aralkyl, aralkyl, phosphonyl, —SO₂R³; —C(O)R⁵; —C(O)OR⁷ or —C(O)NR⁹R¹⁰;

R³; R⁵; R⁷; R⁹ and R¹⁰ are each independently selected from H, substituted lower alkyl, lower alkyl, substituted aralkyl, aralkyl, substituted aryl or aryl; or (B)(ii) a compound, or a protonate or salt thereof, having a structure represented by:

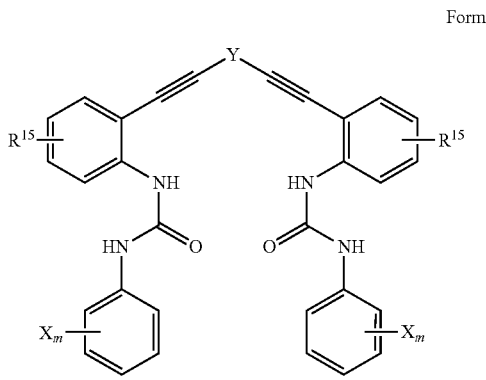

Formula II wherein Y is

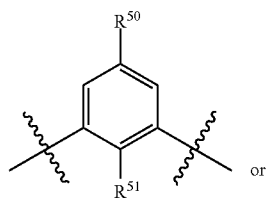 or 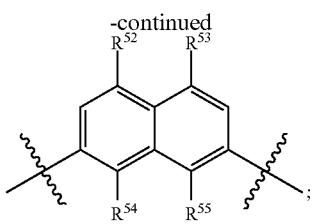;

wherein $R^{50}$, $R^{51}$, $R^{52}$, $R^{53}$, $R^{54}$ and $R^{55}$ are each independently selected from hydrogen, alkyl, substituted alkyl, a polyether moiety, carboxyl, substituted carboxyl, carbamate, substituted carbonate, carbonyloxy, alkoxy, substituted alkoxy, haloalkyl, halogen, nitro, amino, aryloxy, cyano, hydroxyl, or sulfonyl;

each $R^{15}$ is independently H, alkyl, substituted alkyl, a polyether moiety, carboxyl, substituted carboxyl, carbamate, substituted carbonate, carbonyloxy, alkoxy, substituted alkoxy, haloalkyl, halogen, nitro, amino, amido, aryloxy, cyano, hydroxyl, or sulfonyl;

each X is independently halogen, alkoxy, substituted alkoxy, alkyl, substituted alkyl or a polyether moiety; and m is 0 to 5.

10. The device of claim 9, wherein the polymer is selected from at least one of a polyvinyl chloride, polyvinyl alcohol, polystyrene, butadiene copolymer, polysiloxane, epoxy acrylate, methacrylate, urethane acrylate, polyacrylamide, or a combination thereof.

11. The device of claim 10, wherein the polymeric element further comprises at least one ionophore.

12. The device of claim 9, wherein the polymeric element further comprises at least one 7etraalkylammonium salt.

13. The device of claim 9, wherein (B)(i) or (B)(ii) is present in the polymeric element in an amount of 0.1 to 5% by weight, based on the total weight of the polymeric element.

14. The device of claim 9, wherein the polymeric element comprises (B)(i).

15. The device of claim 9, wherein the polymeric element comprises (B)(ii).

* * * * *